United States Patent
Yudelman

[19]

[11] Patent Number: 5,957,942
[45] Date of Patent: Sep. 28, 1999

[54] ORAL HYGIENE DEVICE HAVING PLAQUE COLLECTION AND QUANTIFICATION CAPABILITIES

[75] Inventor: Clifford A. Yudelman, 1625 Valdes Dr., La Jolla, Calif. 92037

[73] Assignees: Clifford A. Yudelman; Gillian C. Yudelman, both of Imperial Beach, Calif.; Co-Trustees U.T.D. August 14, 1992.

[21] Appl. No.: 08/915,133

[22] Filed: Aug. 20, 1997

[51] Int. Cl.[6] .................................................. A61B 17/24
[52] U.S. Cl. .......................... 606/161; 606/160; 606/162; 606/167
[58] Field of Search .................................... 606/161, 162, 606/160, 167

[56] References Cited

U.S. PATENT DOCUMENTS

| | | | |
|---|---|---|---|
| 1,811,775 | 6/1931 | Barkwill . | |
| 1,891,864 | 12/1932 | Barrett . | |
| 2,491,274 | 12/1949 | McNeill | 606/161 |
| 5,217,475 | 6/1993 | Kuber | 606/161 |
| 5,217,476 | 6/1993 | Kuber . | |
| 5,226,197 | 7/1993 | Nack et al. | 606/161 |
| 5,735,864 | 4/1998 | Heisinger, Jr. | 606/161 |

FOREIGN PATENT DOCUMENTS

| | | |
|---|---|---|
| 09051898 | 2/1997 | European Pat. Off. . |
| 591498 | 1/1934 | Germany . |
| 773038 | 4/1957 | United Kingdom . |
| 2260905 | 5/1993 | United Kingdom . |
| WO 97/22307 | 6/1997 | WIPO . |

*Primary Examiner*—Michael Buiz
*Assistant Examiner*—Lien Ngo
*Attorney, Agent, or Firm*—Brown Martin Haller & McClain LLP

[57] ABSTRACT

A dual-use tongue scraper is described, which can be used for routine oral hygiene maintenance and also research collection, quantification and analysis of plaque deposited on a subject's tongue. The scraper includes structure such as protuberances, apertures and porous bodies which collect plaque as it is scraped from a subject's tongue. In some embodiments such structure also arrays the plaque in a manner for visual quantification. The plaque may also be removed from the device for direct measurement and analysis. The method of the device's use for collection, quantification and analysis of plaque, as well as the method of its use for application of compositions to a subject's tongue, are also described.

33 Claims, 1 Drawing Sheet

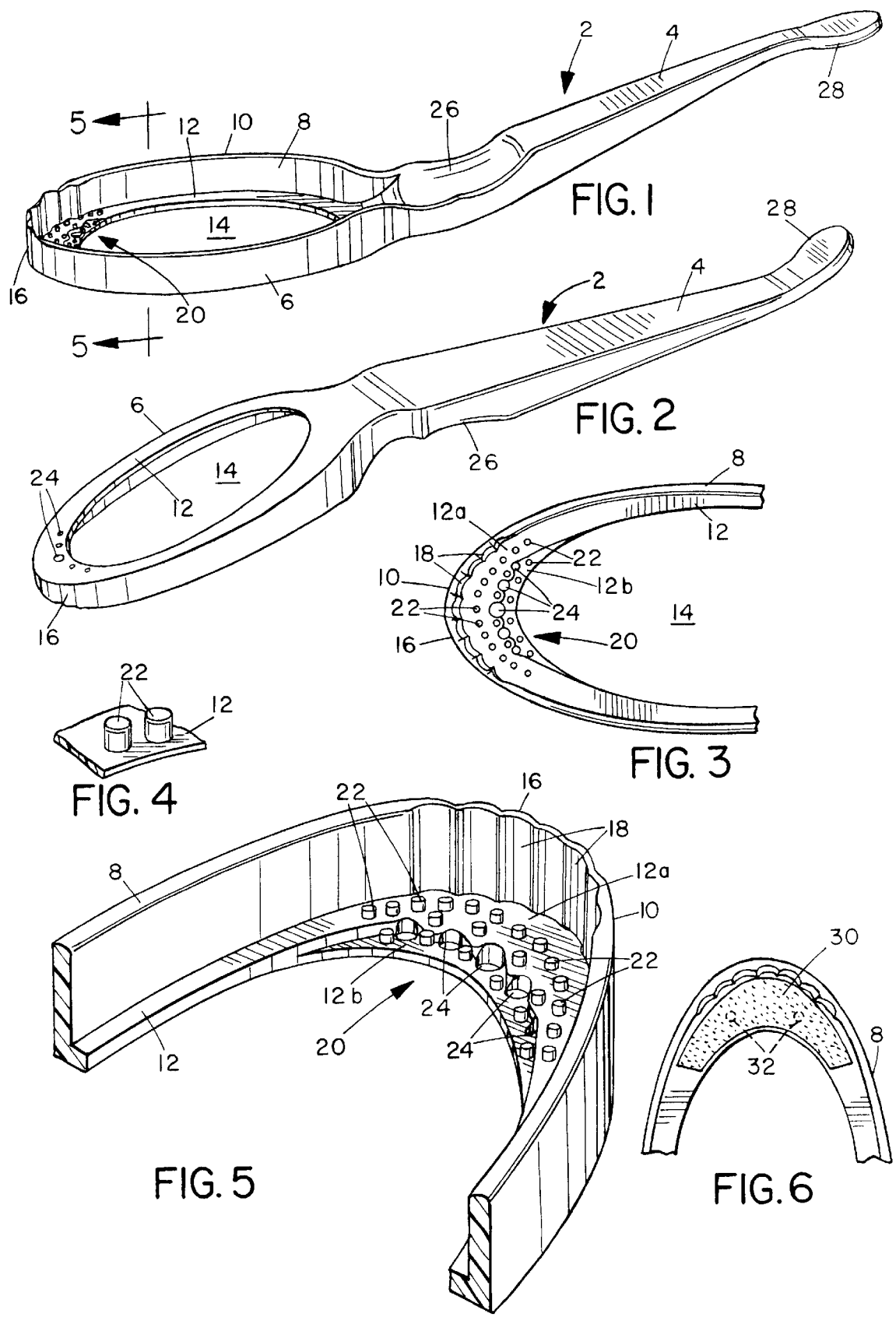

ORAL HYGIENE DEVICE HAVING PLAQUE COLLECTION AND QUANTIFICATION CAPABILITIES

BACKGROUND OF THE INVENTION

1. Field of the Invention

The invention herein relates to oral hygiene devices. More particularly it relates to tongue scrapers.

2. Description of the Prior Art

Dentists and other oral health care providers have known for some time that deposits of plaque on a person's tongue can be a major contributor to oral malodor or "bad breath". Practitioners have therefore strongly recommended to their patients that the patients use tongue scrapers to clean the surface of the tongue each day and remove the plaque before it can accumulate in large quantities and generate the offensive odors. The prior art is replete with patents and literature articles on tongue scrapers and their use, and many such tongue scrapers have been marketed commercially. A example of a typical tongue scraper is disclosed in U.S. Pat. No. 5,217,475 and in the references there described.

Conventional tongue scrapers when properly used are quite adequate for daily hygienic scraping of the tongue surface and removal of plaque to prevent formation of offensive mouth odors. However, the conventional tongue scrapers, such as those described in the above-cited patent, are of little use for serious research on plaque accumulation and oral odor generation. Conventional tongue scrapers provide no means for a researcher to collect useful samples of plaque or to measure plaque accumulation. Techniques such as flushing of the oral cavity are not useful, since such flushing is not specific to the tongue, but rather collects plaque from throughout the oral cavity.

SUMMARY OF THE INVENTION

I have now invented a new and unique type of tongue scraper which is usable not only by the average person for routine oral hygiene maintenance, but which can also be used by researchers to accurately collect and quantify the amount of plaque deposited on a subject's tongue. The device operates in the manner of a conventional tongue scraper, so it can be routinely manipulated and properly used by ordinary persons who wishes to improve their oral hygiene. The plaque collection and quantification structures of the device, however, are sufficiently comprehensive in their ability to collect plaque effectively and to array it in a manner such that a researcher can be assured that a complete and accurate plaque sample has been obtained, that the quantity of plaque is accurately represented, and that the plaque collected is in fact specific to the tongue and not mixed with plaque from elsewhere within the oral cavity. The device permits the plaque to be cleanly removed from the device for precise direct measurement and analysis by the researcher. Additionally, in some embodiments the device also permits rapid visual quantification of the plaque accumulated and collected. In those embodiments where the device provides for ready visual assessment of the plaque quantities, the device also can be used by the lay user to observe his or her own plaque buildup and thus judge the effectiveness of his or her own oral hygiene practices.

Specifically, the scraper of my invention includes a scraping blade, a handle for manipulation by the user and structural devices arrayed behind the scraping blade to collect the plaque as it is scraped from the subject's tongue. The structural devices are appropriately positioned to enable collection of plaque and subsequent ready removal of the collected plaque from the scraper for precise measurement and analysis in appropriate laboratory settings. In some embodiments the structural devices permit an observer (e.g., a researcher or user) to make a rapid and reliable visually assessment and quantification of the collected plaque. The collection structures may be partial physical barriers, such as posts, holes, or the like, or may be collections materials such as sponges, fabric pads, or the like. The scraper of this invention is configured such that all surfaces of the tongue can readily be reached and scraped.

In its broadest form, my invention is of an oral hygiene device comprising a handle having two opposite ends;an elongated scraping blade having two ends and being attached at one of the ends to one of the handle ends;the combination of the handle and the blade having sufficient length to be inserted into a user's mouth and reach to the posterior dorsal surface of the user's tongue; and plaque collection means adjacent the end of the scraper distal from the handle attachment, the plaque collection means being configured to receive and retain plaque dislodged from the user's tongue during operation of the device, and to permit removal of retained plaques for inspection or analysis; such that as the user's tongue is scraped with the device the plaque removed from the tongue is collected and retained.

In preferred embodiments, the plaque collection means is a structure in which the scraper has a base flange extending inside the scraper blade with the actual plaque collection devices arrayed on the flange. Preferably plaque collection devices include a plurality of protuberances projecting from base flange and/or apertures in the base flange. These are conveniently disposed in one or more lines generally paralleling the inner surface of the scraper blade, so that the quantity of captured plaque can be visually observed. Alternatively or porous bodies such as sponges or fabric pads may be attached to the base flange for collection of the plaque for analysis.

The handle may also be shaped to conform to a user's hand and fingers, to facilitate the scraper's use and to help insure that the user will use it properly.

In one method aspect, the invention herein involves a method for the collection and quantification of plaque deposited on a subject's tongue which comprises scraping the subject's tongue with an oral hygiene device as in claim 1 to remove plaque therefrom; collecting the plaque in the collection means of the device; and determined at least the approximate quantity of the collected plaque by visual observation of the disposition of the plaque within the collection means. Preferably in this method aspect the collection means comprises a plurality of protuberances or apertures disposed in an array, and the reference to the disposition of the plaque comprises observation of the extent to which the plaque is dispersed throughout the array.

In another method aspect, the invention involves a method for the collection and analysis of plaque deposited on a subject's tongue which comprises scraping the subject's tongue with an oral hygiene device as in claim 1 to remove plaque therefrom; collecting the plaque in the collection means of the device; removing the collected plaque from within the collection means; and analyzing removed plaque for at least on predetermined property of the plaque. For instance, one property for which one frequently analyzes plaque is the presence or absence in the plaque of anaerobic bacteria which produce volatile sulphur compounds.

In yet another method aspect the collection protuberances of the device may also be used to administer compositions of different types, such as medications, directly to the tongue surface, when it is desired to avoid having such compositions come into contact with teeth, buccal surfaces, etc.

BRIEF DESCRIPTION OF THE DRAWINGS

FIG. 1 is a perspective view of a tongue scraper of the present invention, as viewed with the underside turned upward.

FIG. 2 is a perspective view of the tongue scraper of FIG. 1, as viewed with the upper side turned upward.

FIG. 3 is a partial plan view of the underside of the front end of the tongue scraper of FIGS. 1 and 2.

FIG. 4 is a detail perspective view of two of the plaque collection posts.

FIG. 5 is a cross-sectional perspective view taken generally on the line 5—5 in FIG. 1.

FIG. 6 is a view similar to that of FIG. 3, showing alternative means for collecting plaque samples.

DETAILED DESCRIPTION AND PREFERRED EMBODIMENTS

The invention is best understood by reference to the drawings, particularly FIGS. 1 and 2 for the overall description of the device.

The tongue scraper 2 is in the form of an elongated generally spoon-shaped device having a handle 4 and a scraper blade 6. The handle 4 and the blade 6 may be aligned in any orientation which will facilitate use of the scraper 2. In the embodiment shown in FIGS. 1 and 2, the alignment is a generally coaxial longitudinal alignment with the blade 6 extending directly from the one end of the handle 4. However, it is anticipated that in many configurations other alignments will be used, and there may be various angular offsets of the blade 6 from the handle 4 to facilitate the user or researcher being able to reach far back into the mouth to scrape the plaque from the posterior dorsal surface of the tongue as well as from the portion of the tongue's surface closer to the lips. The handle 4 may also have various configurations to assist the user in holding the scraper 2 for effective use. For instance, in FIGS. 1 and 2 it will be observed that the blade 6 is angled slightly downwardly from the handle 4 (directions being as viewed in FIG. 2 from the "top" side of the device) and that the handle 4 is formed with several formed portions, which will be discussed below.

The blade 6 will have a generally elliptical or oval shaped form, also to facilitate reaching the base of the tongue for scraping. The particular shape will be a matter of choice, and will often be determined by the type of research to be done with the device and/or by the dimensions of the subject's oral cavity. Since humans differ substantially in their oral cavity sizes and shapes, it is anticipated that a research program may well use tongue scrapers of this invention of a number of different sizes and shapes. I have found that a particularly useful device is one with an elliptical blade and a handle of the configuration generally shown in FIGS. 1 and 2. In this embodiment the elliptical blade has a major axis of approximately 66 mm and a minor axis of approximately 30 mm and is attached to a configured handle of approximately 20 cm in length.

The scraper blade 6 of the present invention is formed of an upright wall portion 8 which in use will be aligned perpendicularly to the tongue surface (not shown) with a scraping edge 10 in contact with the tongue surface. At the other end of the wall 8 a base flange 12 projects inwardly from the elliptical blade 6. The flange 12 preferably extends peripherally completely around the inside of the wall 8 to provide structural and shape stability to the wall 8, but leaves a large opening 14 at the center of the blade portion. The opening 14 serves several purposes: it allows the researcher or user to see the tongue surface through the scraper and thus precisely place the scraper on the tongue, it reduces the tendency to cause a gagging reflex in those subjects who have a tendency to gag, it facilitates cleaning of the device after use and it permits the flow of saliva away from the device when it is in use in the subject's mouth.

On the inner surface of the wall 8 at the "front" end 16 of the device are preferably a plurality of scalloped indentations 18 which extend around the arch of the front end 16. The scalloped indentations have significant value, in that they enhance the tongue cleaning effect of the scraper as compared to the effect achieved with a straight, non-scalloped inner surface or edge. Preferably the outer surface of the wall 8 is smooth throughout its entire length, and does not contain corresponding indentations or scallops. For ease of manufacture and effective use, it is preferred that the indentations 18 extend from the scraping edge 10 to the flange 12. The device will work quite satisfactorily, however, even if the indentations 18 do not extend from the scraping edge 10 all the way to the flange 12.

The flange 12 over most of its length will be a single layer structure. In one version, this structure can continue as a single layer all the way around the wall 8; including the portion of the flange 12 adjacent to the front end 16. More preferably, however, as in the example shown in the Figures, the portion of the flange 12 adjacent to the front end 16 will have more than one level, as exemplified by the two levels shown in the illustrated embodiment. In this embodiment, the upper level (designated 12a) is an extension of the rest of the flange 12, while the lower level 12b is formed by either molding or cutting to provide a slightly recessed level, as best seen in FIG. 5. The presence of two levels is believed to enhance the collection and quantification functions of the device, but it will be understood that the device is anticipated to work quite well in either configuration and that the particular configuration (or number of levels) present will be merely a matter of choice to the user or researcher.

On the portion of the flange 12 (or 12a/12b) adjacent to the front end 16 of the device will be structure for trapping and collecting the plaque scraped from the user's tongue by the scraping edge 10, particularly with the aid of the indentations 18. The structure will also be such that the amount of plaque trapped and collected can readily be visually quantified and can also be easily removed from the device for accurate measurement and analysis. In the preferred embodiment shown, the collection structure 20 is formed of a plurality of small protuberances or posts 22 which are spaced, preferably in one or more lines, parallel to the wall 10 (as best seen in FIG. 3) and which are present on the single level 12 or both of the plurality of levels 12a and 12b (as seen in FIGS. 4 and 5). Preferably interspersed with posts 22 and forming a line of their own are a smaller plurality of apertures 24 which are cut or molded completely through the thickness of the flange 12 (or 12a or 12b). The posts 22 are quite small, generally being only about 1 mm in height and diameter. All the posts 22 can be of the same dimensions or they can be of varying dimensions as, for instance, with larger posts near the center adjacent front 16 where most of the plaque will tend to accumulate, with smaller posts at the outer ends of the lines. Similarly, the holes may be of the same or different sizes, with the larger holes toward the center of the array as best seen in FIGS. 2 and 3. The holes are the same general dimensions as the posts, with the larger diameters being approximately 1 mm. In the example device whose overall dimensions were described above, the maximum width of the flange 12 (the sum of the width of partial flanges 12a and 12b) is 7 mm adjacent center 16, tapering to a width of approximately 1 mm at the mid point of the elliptical blade 6. The wall 8 of the blade 6 itself has an average thickness of approximately 1.5 mm, but is reduced at the front end 16 by approximately ½ to ⅔ due to the depth of the indentations 18.

The handle 4 may be in the form of a simple straight shank or it may configured for comfort of the user's hand and/or to cause the user handle in a proper manner and orientation. One preferred handle 4 is shown in the FIGS. 1 and 2 and is of the latter type, with a depression or curved portion 26 formed therein to serve as a thumb rest and force the user to hold the device in the preferred orientation for optimum tongue scraping. The slightly angled offset of the end 28 of the handle is configured to rest against the inside of the user's third and fourth fingers, also to aid in grasping the device in the preferred manner.

The tongue scraper of the present invention may be made of any suitable material which is nontoxic and not otherwise harmful to the user, and not adversely affected by oral cavity fluids, plaque, laboratory flushing or cleaning solutions, or common household cleaners. Metals such as stainless steel or aluminum are quite suitable. However, for economy and ease of manufacture, it is preferred to mold the device from any of a number of common plastic materials, including but not limited to ABS (acrylonitrile-butadiene-styrene), polypropylene, polycarbonate or similar thermoplastic or thermosetting polymeric materials. The device will be fairly rigid to ensure that thorough scraping takes place, but it should have some small amount of flexibility to accommodate the user's hand motions and also to resist breakage if dropped or otherwise subjected to routine impact. It is strongly preferred that the material of which it is made, whether plastic or metal, be essentially smooth and nonporous so that plaque or oral cavity fluids cannot penetrate into the device itself. The presence of such materials deposited in pores of the device will not only affect research by making some of the collected plaque inaccessible, but will also compromise the sterility and ability to clean the device thoroughly for reuse. The presence of such retained plaque will also eventually cause the device itself to become malodorous.

The manner of the device's use will be evident from the description of the structure itself. The user, whether a person merely scraping his/her tongue for ordinary hygienic reasons or a subject participating in a plaque collection program, places the blade end of the device in his or her mouth and scrapes across the tongue to loosen and collect the deposited plaque. The front end 16 of the device is placed sequentially at various locations across his or her tongue, certainly including the farthest back in the mouth and toward the base of the tongue that one can reach, and at each location the device is then pulled toward the lips, thereby scraping over the surface of the tongue so that the plaque is dislodged from the tongue surface and accumulated inside the inner part of the wall 10 adjacent to the front end 16 of the wall. The normal movement of the device and of the plaque being scraped forces the plaque along the indentations 18 and into contact with the posts 22 and holes 24, which trap and accumulate the plaque as the scraping continues. For ordinary hygienic use, once the tongue surface has been completely scraped one or more times, the device is removed from the mouth and rinsed and cleaned for subsequent use, in the manner of conventional tongue scrapers. With the unique structure of the present tongue scraper for use for research purposes, however, once the scraping has been completed the device is presented without rinsing or cleaning to the researcher or other observer who can visually inspect the amount, appearance and odor of the accumulated plaque present in the collection zone 20 among the posts 22 and holes 24. A simple visual assessment can readily be made, such as by observing that the quantity of plaque is such to have reached the first row of posts 22 adjacent to the inside of the wall 8 or, for instance, is a larger quantity which has extended beyond to a second row of posts or a row of holes. Thus relative accumulations of plaque can be designated by the distance that the plaque has reached to specific rows of posts or holes distal to the inner surface of the wall 10. The number of rows of holes and/or posts, as noted, may be different in various embodiments of the device, so as to form a set of graduated devices, whose extent will be determined by the amount of accumulated plaque expected to be gathered by each test from individual subjects. For example, in a test program variables may include the number of uses per day, the number of days of use per week, the times of day of use, and so forth, so that the researcher will anticipate that different subjects will have different collected amounts of plaque based on their assigned scraping schedule and provide the subjects with variously configured tongue scrapers having the appropriate number of posts and/or holes for a particular subject's test protocol.

Visual quantification will be, to a certain extent, subjective. Depending on the purpose of the researcher's work, such subjective measurements and relative comparisons may be quite adequate. However, if more accurate measurements are required, the present device is ideally suited for retaining the collected and accumulated plaque in position without loss until the researcher can flush the plaque from the device into an appropriate laboratory measuring vessel for actual measurement of the quantity of plaque obtained. Flushing agents such as water, alcohol, hydrocarbon solvents or the like are well known and need not be further described here. Similarly, methods for accurate measurement of quantities of plaque are also well known and need no further description. Of course, the accumulated plaque can also be analyzed for composition, presence of microorganisms or viruses, etc. once collected at the laboratory. For instance, one will normally test for the presence in the plaque of anaerobic bacteria known to produce volatile sulphur compounds, which contribute to oral malodor.

While the collecting structure 20 has been described in terms of posts and holes, it will be evident that there are numerous other types of small structures which will work equally well. Small conical protuberances or projections, rounded mound-like projections, circular or elliptical holes and numerous other similar structures will readily be apparent to those skilled in the art. Similarly, the specific patterns in which the various post holes or other structures can be arrayed may vary from the simple lines shown in FIG. 3 to the more random arrangement shown in FIG. 5. Lines can have various lengths and the trapping structures can be concentrated in some areas and more dispersed in other areas, usually with the greater concentrations being at the front of the blade area. While there is nothing to prevent having trapping structures also located elsewhere around the flange 12 in addition to (or even instead of) adjacent to the front end 16, it is generally found that with normal scraping techniques there is usually little or no plaque collected in the side areas of the device and therefore little need to have trapping devices in those locations. Of course, if a different scraping pattern is to be used, such as one in which the researcher wants the scraping device to be moved laterally rather than longitudinally, the positioning of the collection structures will be dispersed accordingly. Those skilled in the art will be readily able to define the optimum configuration for the particular research involved.

Other embodiments are illustrated in FIG. 6. In one embodiment, a small number of protuberances 32, preferably with a pointed or barbed structure, are part of the flange 12. A sponge, cotton pad or similar porous body of material 30, configured to conform to the shape of the front end of the device and to collect plaque, is impaled on the protuberances 32. The scraper 2 is then used in its normal manner, and the removed plaque is collected on the surface of and within the porous body 30. The porous body 30 is then removed for plaque analysis, the scraper is cleaned, and a new porous body 30 attached. Alternatively, in another embodiment the flange 12 is smooth, without protuberances 32, and the porous body 30 is adhered directly to the flange 12 by a suitable releasable adhesive (not shown). In the latter embodiment, care must be taken that traces of adhesive do not remain on the flange 12 after a used body 30 is removed, since any plaque held by such residual adhesive will be a contaminant for subsequent plaque samples.

Similarly, the handle may be of a variety of different configurations if different scraping techniques are to be used. Those skilled in the art of tongue scraping will be readily able to determine the best handle configuration for the techniques to be used.

In addition to its primary use as a scraper, the device of the present invention may also be used to administer commercial toothpastes or medicated toothpastes, or other similar medicated compositions, directly to the tongue surfaces, particularly the posterior dorsal surface. Typical medications which can be administered in this manner include chlorhexidene gluconate and zinc chloride, both of which have been found effective against oral malodor, especially that caused by anaerobic bacterial-produced volatile sulphur compounds. Commonly this administration will be done immediately after scraping the tongue clean. The scraper is cleaned and a quantity of the toothpaste or other composition is applied to the scraper, to be held in place by the composition's own slight adhesive character, and also by contact with the various posts 22. The scraper is then inserted into the mouth and brought into contact with the desired areas of the tongue surface, so that the toothpaste or other composition can be transferred to the tongue surface. This manner of use is particularly advantageous, in that it is significantly more effective in reducing or eliminating tongue-caused malodor than is general oral rinsing or administration of the same medications. It also is advantageously used to administer pastes or other compositions directly to the tongue when the material to be administered would be deleterious to the teeth or buccal surfaces if it came into contact with them. For instance, there are some medications which can stain tooth surface enamel. By application of those materials directly to the tongue, tooth contact and resultant tooth staining can be avoided.

It will evident that there are numerous embodiments of this invention which, while not expressly set forth above, are clearly within the scope and spirit of the invention. The above description is therefore to be considered exemplary only, and the actual scope of the invention is to be determined solely from the appended claims.

I claim:

1. An oral hygiene device for scraping a human user's tongue within said user's mouth, comprising:

a handle having two opposite ends;

an elongated scraping blade having two ends and being attached at one of said ends to one of said handle ends;

a combination of said handle and said scraping blade having sufficient length to be inserted into said user's mouth and extend from a point exteriorly of said user's mouth to the posterior dorsal surface of said user's tongue; and plaque collection means adjacent the end of said scraping blade distal from said handle attachment, said plaque collection means being configured to receive and retain plaque dislodged from said user's tongue during operation of said device, and to permit removal of retained plaque for inspection or analysis;

such that as said user's tongue is scraped with said device the plaque removed from said tongue is collected and retained.

2. An oral hygiene device as in claim 1 wherein said scraping blade comprises a curvilinear wall disposed to be moved across the surface of said tongue in a plane perpendicular to said tongue surface and has an inner surface facing toward said handle, an outer surface facing away from said handle, a scraping edge bridging said inner and outer surfaces and disposed to contact said tongue surface during scraping, and a base edge bridging said inner and outer surfaces at the end of said surfaces opposite said scraping edge.

3. An oral hygiene device as in claim 2 wherein at the distal end thereof said inner wall has at least one indentation starting at said scraping edge and extending at least part way to said base edge.

4. An oral hygiene device as in claim 3 comprising a plurality of said indentations.

5. An oral hygiene device as in claim 2 further comprising a base flange extending from said inner surface of said wall at said base edge inwardly toward said handle and having said plaque collection means disposed thereon.

6. A oral hygiene device as in claim 5 wherein said plaque collection means disposed on said flange comprises a porous collection member receives and retains said plaque on its surface and within its pores.

7. An oral hygiene device as in claim 6 wherein said plaque collection means comprises a sponge or fabric pad.

8. An oral hygiene device as in claim 5 wherein said plaque collection means disposed on said flange comprises structure which permits visual observation of said retained plaque and which retains said plaque in a manner which permits at least approximate quantification of the amount of said retained plaque by means of said visual observation.

9. An oral hygiene device as in claim 8 wherein said plaque collection means comprises a plurality of protuberances projecting from said base flange toward said scraping edge.

10. An oral hygiene device as in claim 9 wherein said plurality of protuberances are disposed in at least one line generally paralleling said inner surface of said wall.

11. An oral hygiene device as in claim 9 wherein said quantification is enabled by said protuberances capturing plaque scraped from said tongue, such that the quantity of said captured plaque can be visually observed.

12. An oral hygiene device as in claim 9 wherein said plurality of protuberances are disposed in a plurality of lines each generally paralleling said inner surface of said wall.

13. An oral hygiene device as in claim 12 wherein said quantification is enabled by said protuberances capturing plaque scraped from said tongue, such that the quantity of said captured plaque and the number of said lines having captured said plaque can be visually observed.

14. An oral hygiene device as in claim 5 wherein said plaque collection means comprises a plurality of apertures extending through said base flange.

15. An oral hygiene device as in claim 14 wherein said plurality of apertures are disposed in at least one line generally paralleling said inner surface of said wall.

16. An oral hygiene device as in claim 14 wherein said quantification is enabled by said apertures capturing plaque scraped from said tongue, such that the quantity of said captured plaque can be visually observed.

17. An oral hygiene device as in claim 14 wherein said plaque collection means further comprises, in association with said apertures, a plurality of protuberances projecting from said base flange toward said scraping edge.

18. An oral hygiene device as in claim 17 wherein said plurality of protuberances are disposed in a plurality of lines each generally paralleling said inner surface of said wall.

19. An oral hygiene device as in claim 17 wherein said quantification is enabled by said protuberances and said apertures capturing plaque scraped from said tongue, such that the quantity of said captured plaque and the number of said lines of protuberances and apertures having captured said plaque can be visually observed.

20. An oral hygiene device as in claim 1 wherein said handle is configured to permit manipulation of said device in a manner to direct said scraping blade into contact with an area of the tongue surface such that said area can be readily scraped.

21. An oral hygiene device as in claim 20 wherein said handle is configured to permit gripping by a user's hand in a manner convenient to manipulation by said user to direct said scraping blade into contact with an area of the tongue surface such that said area can be readily scraped.

22. An oral hygiene device as in claim 21 wherein said handle has formed therein guide means directing grasping thereof by said user.

23. An oral hygiene device as in claim 22 wherein guide means comprises depressions formed in said handle to receive at least one of said user's fingers or thumb of the hand holding said device.

24. An oral hygiene device as in claim 1 wherein said scraping blade has a generally elliptical or oval shape with the major axis thereof generally in alignment with said handle.

25. A method for the collection and quantification of plaque deposited on a subject's tongue which comprises:

scraping said subject's tongue with an oral hygiene device as in claim 1 to remove plaque therefrom;

collecting said plaque in said collection means of said device; and determining at least the approximate quantity of said collected plaque by visual observation of the disposition of said plaque within said collection means.

26. A method as in claim 25 wherein said collection means comprises a plurality of protuberances or apertures disposed in an array, and said reference to said disposition of said plaque comprises observation of the extent to which said plaque is dispersed throughout said array.

27. A method for the collection and analysis of plaque deposited on a subject's tongue which comprises:

scraping said subject's tongue with an oral hygiene device as in claim 1 to remove plaque therefrom;

collecting said plaque in said collection means of said device;

removing said collected plaque from within said collection means; and analyzing removed plaque for at least one property of said plaque.

28. A method as in claim 27 wherein said property of said plaque comprises the presence in said plaque of anaerobic bacteria capable of producing volatile sulphur compounds.

29. A method as in claim 27 wherein said collection means comprises porous body which collects said plaque on its surface and within its pores.

30. A method as in claim 29 wherein said porous body comprises a sponge or a fabric pad.

31. A method for application of a composition to the surface of a person's tongue which comprises:

applying a quantity of said composition to an oral hygiene device as in claim 1;

inserting said device having said compositions applied thereto into said subject's oral cavity and positioning said device adjacent a desired location of said tongue; and bringing said device and said composition into contact with said tongue such that at least a portion of said composition is transferred from said device to said surface of said tongue.

32. A method as in claim 31 wherein said device having applied thereto said composition is manipulated within said subject's oral cavity in a manner such that no portion of said composition comes into contact with any surface within said subject's oral cavity other than said surface of said tongue.

33. A method as in claim 32 wherein said composition is applied to a posterior dorsal surface of said tongue.

* * * * *

UNITED STATES PATENT AND TRADEMARK OFFICE
CERTIFICATE OF CORRECTION

PATENT NO. : 5,957,942

DATED : September 28, 1999

INVENTOR(S) : Clifford A. Yudelman

It is certified that error appears in the above-identified patent and that said Letters Patent is hereby corrected as shown below:

Column 7, line 59 following "will" insert --be--.

Claim 6, line 3, following "member" insert --which--.

Signed and Sealed this

Ninth Day of January, 2001

Attest:

Attesting Officer

Q. TODD DICKINSON

Commissioner of Patents and Trademarks